United States Patent [19]
Krejcarek et al.

[11] Patent Number: 5,744,322
[45] Date of Patent: Apr. 28, 1998

[54] AUTOMATED INCUBATING AND IMAGING SYSTEM FOR A DISPOSABLE MICROORGANISM CULTURING DEVICE AND METHOD OF USE

[75] Inventors: Gary E. Krejcarek, White Bear; Patrick A. Mach, Shorewood; Scott D. Morgan, Cottage Grove; Thomas A. Turgeon, Fridley, all of Minn.

[73] Assignee: Minnesota Mining and Manufacturing Company, St. Paul, Minn.

[21] Appl. No.: 646,291

[22] PCT Filed: Dec. 15, 1994

[86] PCT No.: PCT/US94/14515

§ 371 Date: Aug. 29, 1996

§ 102(e) Date: Aug. 29, 1996

[87] PCT Pub. No.: WO95/16768

PCT Pub. Date: Jun. 22, 1995

Related U.S. Application Data

[63] Continuation-in-part of Ser. No. 168,681, Dec. 17, 1993, abandoned.

[51] Int. Cl.[6] ............... C12Q 1/06; C12M 1/34
[52] U.S. Cl. ............ 435/39; 435/286.2; 435/287.3; 435/288.3; 435/288.7; 435/303.1; 435/809
[58] Field of Search ................... 435/29, 30, 34, 435/39, 40, 286.2, 287.3, 287.9, 288.3, 288.7, 305.1, 808, 809, 303.1; 422/63, 65, 66, 104; 40/649, 653; 414/222; 382/128, 133

[56] References Cited

U.S. PATENT DOCUMENTS

| | | | |
|---|---|---|---|
| 822,354 | 6/1906 | Duncan | 40/649 |
| 1,768,715 | 7/1930 | Hopp et al. | 40/649 |
| 3,493,772 | 2/1970 | Daughters, II et al. | 250/222 |
| 3,736,432 | 5/1973 | Sweet | 250/222 PC |
| 3,764,480 | 10/1973 | Jedicka et al. | 195/103.5 R |
| 3,811,036 | 5/1974 | Perry | 235/92 PC |
| 3,972,778 | 8/1976 | Cunningham | 195/139 |

(List continued on next page.)

FOREIGN PATENT DOCUMENTS

| | | | |
|---|---|---|---|
| 0 088 601 | 9/1983 | European Pat. Off. | G01N 35/04 |
| 0 301 600 | 7/1990 | European Pat. Off. | G01N 35/00 |
| 0 397 256 | 11/1990 | European Pat. Off. | G01N 35/00 |
| 0 429 030 | 7/1991 | European Pat. Off. | B01L 7/00 |
| 0 547 709 | 10/1993 | European Pat. Off. | G01N 35/00 |
| 2 602 074 | 1/1988 | France | G06F 15/62 |
| 24 43 410 C3 | 10/1981 | Germany | G06M 11/02 |
| 39 16804 | 11/1989 | Germany | C12Q 1/06 |
| 57-63452 | 4/1982 | Japan | G01N 33/48 |
| 2-6729 | 1/1990 | Japan | G01N 15/14 |
| 1434465 | 10/1988 | U.S.S.R. | G06M 11/02 |
| 2 227 346 | 7/1990 | United Kingdom | G06K 9/62 |
| 94/26926 | 11/1994 | WIPO | C12Q 1/04 |

OTHER PUBLICATIONS

"Count Up to 1000 Objects In A Field, Automatically", by Artek Systems Corporation (3 pages) no date provided.
"Electronic Colony Counters" by VSMF (3 pages) no date provided.

*Primary Examiner*—William H. Beisner

[57] ABSTRACT

An apparatus for counting microorganism colonies on at least on disposable microorganism culturing medium having a substantially planar substrate. The apparatus has an imaging system for detecting colonies on the substantially planar substrate, and a holder positioning device for storing and queuing one or more holders, each adapted to support one of the substrates. The positioning device moves the holders sequentially into a predetermined position relative to the imaging system so that images can be obtained. The imaging system cooperates with a counting device for counting the colonies using information from several images provided by the imaging system taken at different times as the positioning device cycles the holders past the predetermined location to be imaged. Suitable holders, and a method of queuing and counting colonies on substrates, are also disclosed.

9 Claims, 10 Drawing Sheets

U.S. PATENT DOCUMENTS

| | | | |
|---|---|---|---|
| 4,116,775 | 9/1978 | Charles et al. | 195/103.5 M |
| 4,118,280 | 10/1978 | Charles et al. | 195/127 |
| 4,456,380 | 6/1984 | Kondo et al. | 356/418 |
| 4,535,239 | 8/1985 | Brighton | 250/339 |
| 4,554,867 | 11/1985 | Thumm | 100/3 |
| 4,565,783 | 1/1986 | Hansen et al. | 435/299 |
| 4,637,053 | 1/1987 | Schalkowsky | 382/6 |
| 4,720,463 | 1/1988 | Farber et al. | 435/291 |
| 4,896,966 | 1/1990 | Boisseau et al. | 356/442 |
| 5,117,467 | 5/1992 | Misaki et al. | 382/6 |
| 5,403,722 | 4/1995 | Floeder et al. | 435/39 |
| 5,510,246 | 4/1996 | Morgan | 435/39 |

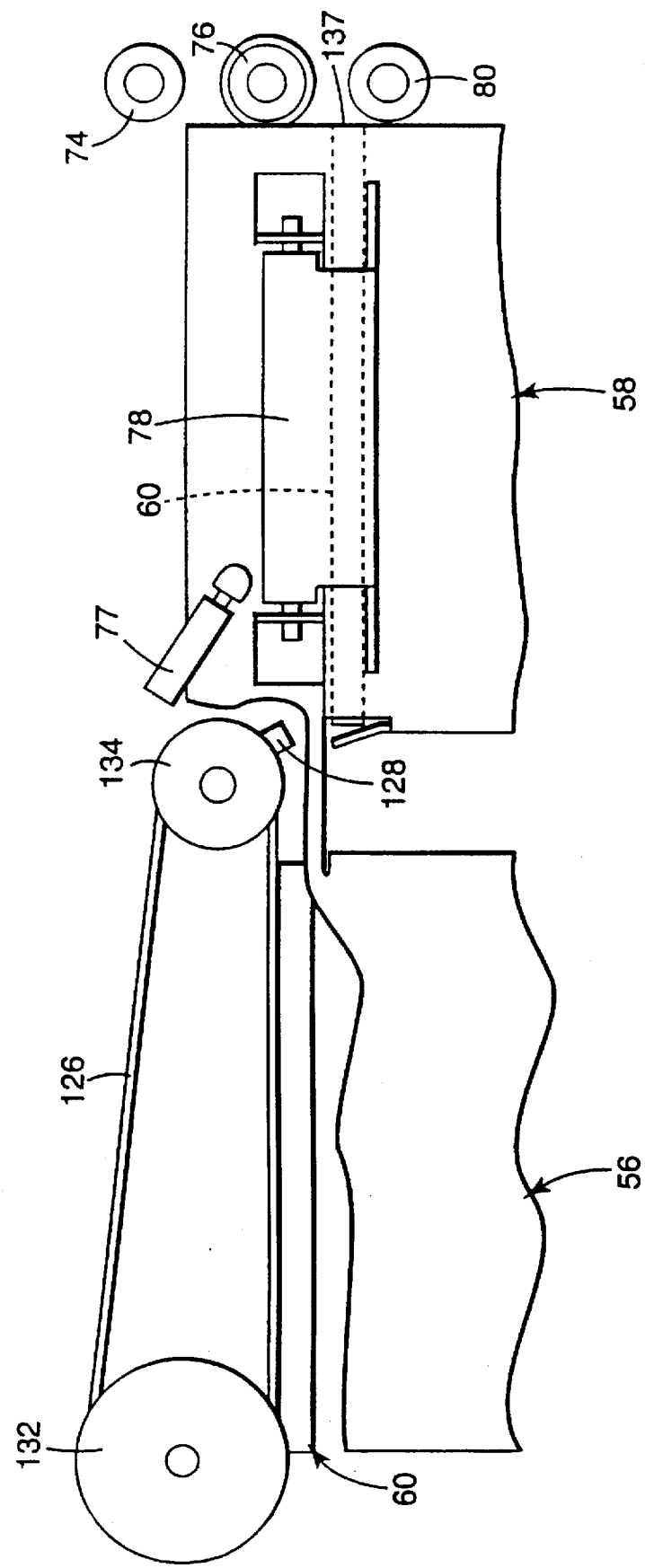

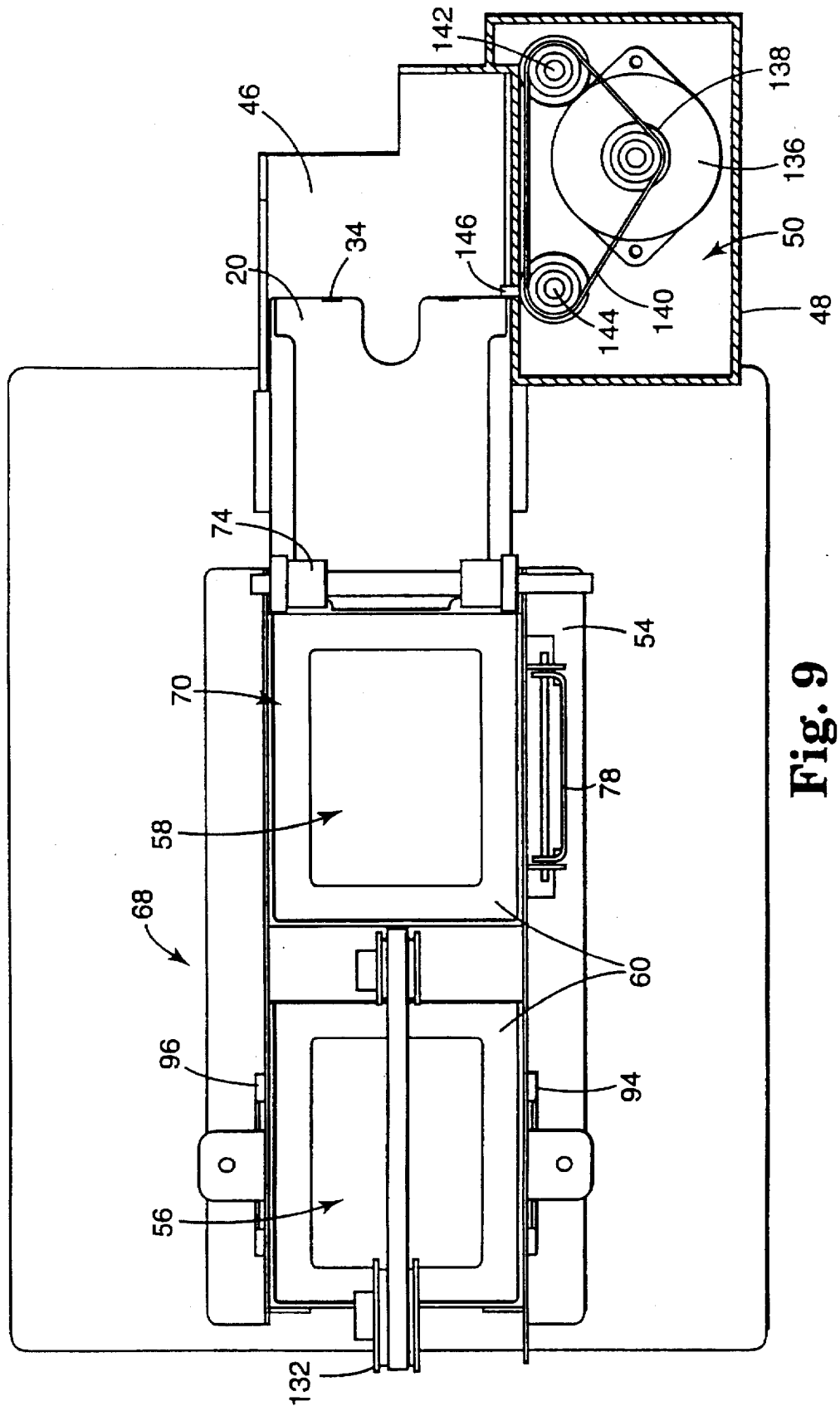

AUTOMATED INCUBATING AND IMAGING SYSTEM FOR A DISPOSABLE MICROORGANISM CULTURING DEVICE AND METHOD OF USE

This application is a continuation-in-part of U.S. patent application Ser. No. 08/168,681, filed Dec. 17, 1993, now abandoned.

TECHNICAL FIELD

This invention relates to a method and apparatus for queuing and moving multiple similar objects for imaging particularly to allow counting a number of distinct elements in the images so obtained. In particular, it relates to microbiological testing and improvements in the handling and reading of disposable microorganism culturing devices.

BACKGROUND OF THE INVENTION

Different methods and devices are known for counting microorganism colonies in, for example petri dishes or in disposable microorganism culturing devices such as PETRIFILM culture plates, manufactured by Minnesota Mining and Manufacturing Company, St. Paul, Minn. (3M). In the latter case, such devices have a very thin layer of growth medium, making all colonies visible with surface illumination. Manual counting of colonies on such a culture plate by trained laboratory personnel is well-known; typically a plate will be inoculated and marked as to the source of the inoculant, stacked together with similar samples, and placed into an incubator. A manual inspection and counting is typically performed after a period of about 24 hours. This method has known disadvantages, particularly the costs associated with the use of skilled technicians to perform the time-consuming task of manual counting, as well as the limited accuracy of the counts achieved.

Also desirable in the matter of microbiological counting is the early detection of colonies, particularly when food products are being tested. If food product samples indicate excessive contamination, the product must often be discarded. Reliable early detection of excessive contamination in the range of 6 to 12 hours after inoculation would be welcomed because it would allow identification of contaminated products early in processing, thereby avoiding additional expenses incurred in processing product that will be discarded and possibly contaminating additional product by running it through contaminated processing equipment.

U.S. patent application Ser. No. 08/061,678, filed May 14, 1993, METHOD FOR THE EARLY DETECTION OF COLONY GROWTH, now U.S. Pat. No. 5,510,246, reports improvements in colony counting in, e.g., a disposable microorganism culturing media having a substantially planar substrate. These include scanning and imaging the inoculated surface more than once and processing the images to produce a scaled time lapse image. Processing this scaled time lapse image allows the identification of hit pixels which can be clustered to identify the appearance of colonies. Thus early indication of colony growth may be obtained.

U.S. patent application Ser. No. 08/272,996, filed Jul. 14, 1994, A TECHNIQUE TO COUNT OBJECTS IN A SCANNED IMAGE, now U.S. Pat. No. 5,403,722, reports a method and an apparatus for automated counting. However, a limitation on the reported apparatus is the physical properties of the disposable microorganism culturing media. The disposable culturing media would be difficult to manipulate and index for accurate imaging over repeated cycles. U.S. patent application Ser. No. 08/240,846, filed May 11, 1994, CASSETTE FOR DISPOSABLE MICROORGANISM CULTURING MEDIA AND AUTOMATED SCANNING SYSTEM, now U.S. Pat. No. 5,573,950 reports an apparatus adapted to automated counting of disposable culturing media.

SUMMARY OF THE INVENTION

The present invention overcomes the above identified limitations by allowing planar substrates to be more accurately monitored under automatic control. In one aspect, the invention includes an apparatus for counting microorganism colonies on at least one disposable microorganism culturing medium having a substantially planar substrate. Each of these substrates is adapted to be held and supported within a holder. The apparatus has an imaging means for detecting colonies on the substantially planar substrate. Cooperating with the imaging means is a holder positioning means for storing and queuing one or more of the holders. The holder positioning means is adapted for moving the holders sequentially into a predetermined position relative to the imaging means so that images can be obtained. The imaging means cooperates with a counting means for counting the colonies using information from several images provided by the imaging means taken at different times as the positioning means cycles the holders past the predetermined location to be imaged.

A preferred holder for supporting the substantially planar substrates is conveniently made with a generally planar bottom having a side wall attached thereto. The side wall has an overhanging portion parallel to said bottom for removably restraining the substantially planar substrate adjacent to the bottom of the holder. In a particularly preferred embodiment, the side wall has a gap positioned so as to facilitate placing the substantially planar substrate between the bottom and the overhanging portion. Conveniently, one or more projections are provided, attached to the bottom, positioned where the stiffness of the substantially planar substrate urges it into a position so as to be restrained within said holder, but where the substantially planar substrate may be bent to permit withdrawal of the substantially planar substrate from the holder over the projection. To facilitate such bending of the substantially planar substrate, it is preferred to provide a cut-out within the bottom adjacent to the gap in the side wall.

The holder positioning means includes a frame defining a first queuing area and a second queuing area. These queuing areas will conveniently be sized to support and contain a stack of the above described holders. In preferred embodiments each of these holders will be supported within the stack in a tray which is sized to closely, but not bindingly, receive the holder. A hoist means is provided for lifting the stack of trays within the first queuing area, and a detent means is provided adjacent the hoist means so that the stack within the first queuing area may be lifted and held temporarily. A first conveyor means is provided for displacing a tray at the bottom of a stack within said second queuing area to the bottom of the first queuing area into the space provided when the rest of the stack of trays within the first queuing area is being held in a raised position by the detent means. A second conveyor means is provided for moving a tray at the top of a stack of trays within the first queuing area to the top of said second queuing area. A motive means is provided for operating the various mechanical expedients above described in the proper order and manner to accomplish the task of moving trays bearing the appropriate holder to the predetermined position when required for imaging.

To facilitate the use of the apparatus, the holder positioning means will also have means for inserting an additional holder into an empty tray within the stack of trays supported by the frame, and means for removing a selected holder from a tray within the stack. In a preferred embodiment, the frame will be enclosed within an incubator, and the insertion and removing means will operate through the incubator enclosure.

The imaging means includes a light source producing light striking an upper surface of a substantially planar substrate which is in a holder in the predetermined position. Conveniently, a video camera will be positioned so as to view a substantially planar substrate which is in a holder in that predetermined position.

In a second aspect, the invention includes a method of counting microorganism colonies on at least one disposable microorganism culturing medium having a substantially planar substrate. The method includes at least the steps of:

a) providing one or more holders adapted to support the substantially planar substrates;

b) queuing and moving the holders sequentially into a predetermined position;

c) imaging the substantially planar substrates in that predetermined position and storing information about the images so obtained;

d) comparing images taken from each one of said substantially planar substrates at two or more predetermined times; and e) providing a count of microorganism colonies on each of the substantially planar substrates using the information obtained from the comparisons. In most contemplated uses, the method will also include the step of incubating the substantially planar substrates between the predetermined times.

In a third aspect, the invention may be considered to be related to the holder described above per se, with it's special utility in supporting the substantially planar substrates.

A feature of the invention is the use of holders for substantially planar substrates, and a frame with trays to manipulate and queue the holders.

An advantage of the invention is that a more accurate indication of colony appearance may be obtained at an earlier time, with more of the testing functions being performed automatically.

BRIEF DESCRIPTION OF THE DRAWINGS

A more complete understanding of the invention and its advantages will be apparent form the Detailed Description taken in conjunction with the accompanying Drawings, in which:

FIG. 8 is a cut-away side view of the area depicted in FIG. 7;

FIG. 9, is a cut-away top view of the area depicted in FIG. 8;

DETAILED DESCRIPTION

Figure 1:
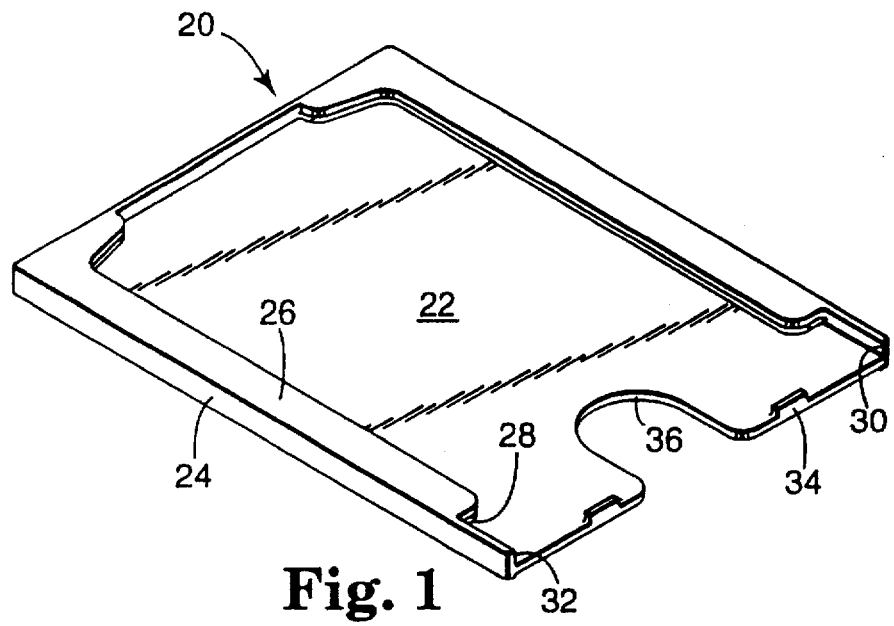
FIG. 1 is a perspective view of a holder according to the present invention, suitable for supporting a disposable microorganism culturing medium having a substantially planar substrate.
Figure 2:
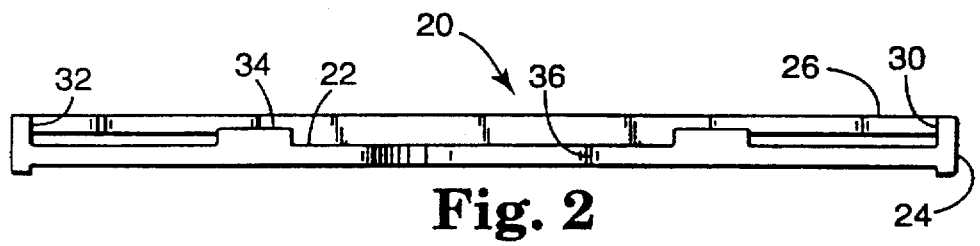
FIG. 2 is a top plan view of the holder of FIG. 1.
Figure 3:
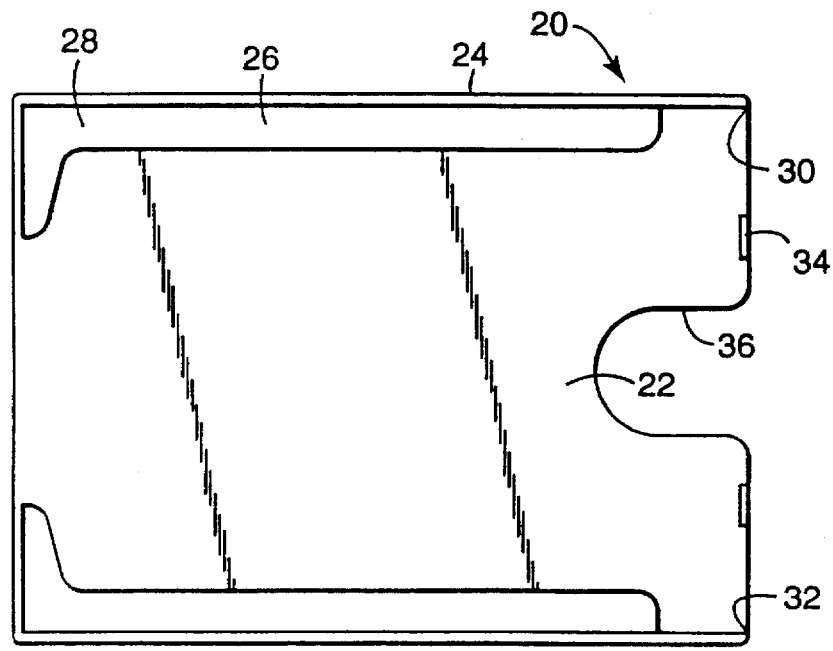
FIG. 3 is an end view of the holder of FIG. 1.

Referring to FIG. 1, a perspective view of a holder 20 according to the present invention is illustrated. The holder 20 is adapted for supporting a disposable microorganism culturing medium having a substantially planar substrate 21 (shown in FIG. 11), and has a generally planar bottom 22. Rising from the bottom 22 is a side wall 24 for retaining the substantially planar substrate over the bottom. Side wall 24 has an overhanging portion 26 parallel to the bottom 22 for further restraining the substantially planar substrate. It will be observed that the bottom 22 conveniently has openings 28 positioned under the overhanging portion 26 which facilitates the injection molding of the depicted embodiment. It will also be observed that the side wall 24 extends slightly below the bottom 22 all around. This allows several advantages: frictional force is reduced when it is desired that the holder 20 be ejected from the apparatus, air is allowed to circulate under the holder, allowing a more consistent incubation of the substantially planar substrate 21, and less plastic dust is generated by repeated sliding of the holder in and out of the apparatus. Such dust can accumulate and make the counting of colonies more difficult.

The side wall 24 has ends 30 and 32 defining a gap in the side wall positioned so as to facilitate sliding the substantially planar substrate between the bottom 22 and the overhanging portion 26. A pair of projections 34 are attached to the bottom 22. Conveniently, the substantially planar substrate to be used with holder 20 has a certain stiffness which urges it into a position so as to be restrained within the holder, bound between bottom 20, side walls 24, overhanging portion 26, and projections 34. However, preferred substantially planar substrates are not so stiff as to resist an operator bending one slightly so as to clear projections 34, permitting the substantially planar substrate to be withdrawn from holder 20. In order to facilitate bending of the substantially planar substrate by an operator, holder 20 is conveniently constructed with a cut-out 36 in the bottom 22.

Figure 4:
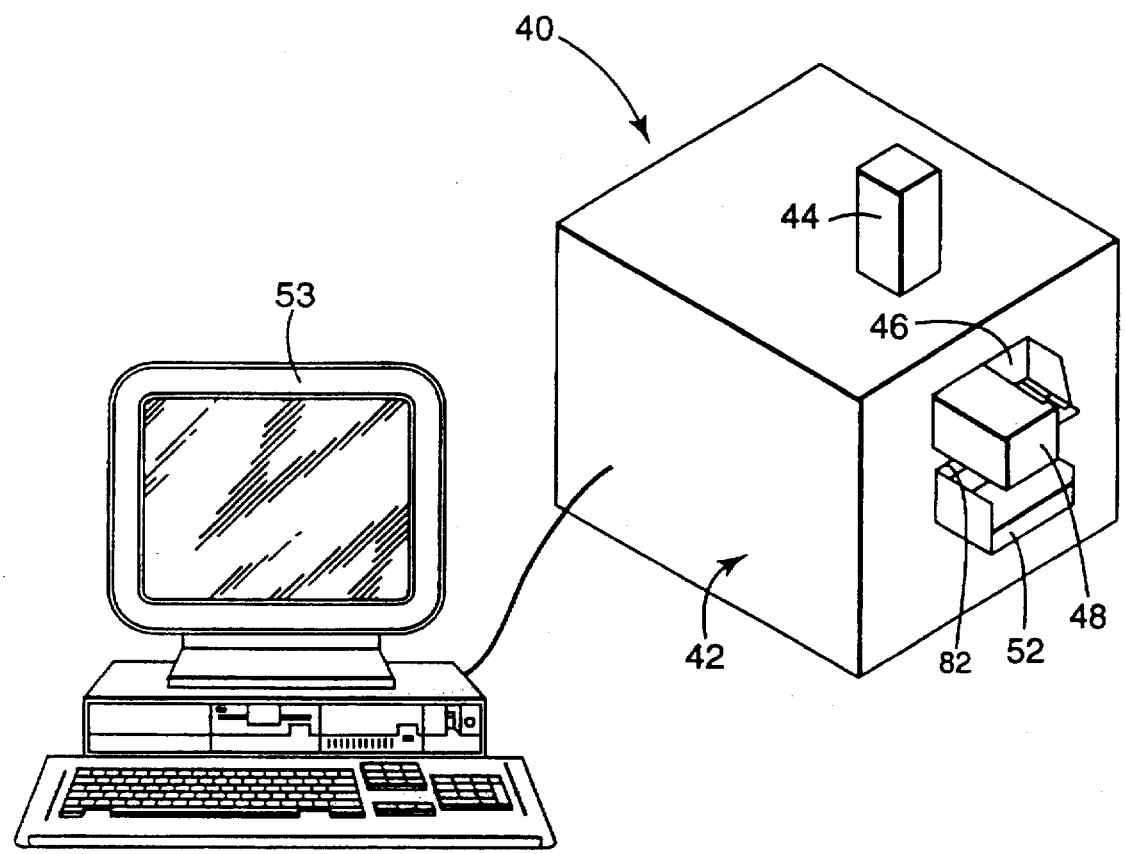
FIG. 4 is a perspective view of an apparatus for counting microorganism colonies according to the present invention.

Referring to FIG. 4, a perspective view of an apparatus 40 for counting microorganism colonies according to the present invention is illustrated. The apparatus 40 includes an incubator enclosure 42, which has mounted on it an enclosure 44 for the imaging system, a shelf 46 adapted for supporting holders which are to be inserted into the incubator enclosure, an enclosure 48 for an input mechanism 50 (seen in FIG. 8) for introducing holders on the shelf 46 into the incubator enclosure 42, and a hopper 52 for receiving holders that have been ejected from the incubator enclosure. An alternative input means, not illustrated, includes a cartridge capable of containing a plurality of holders in a stack. Such a cartridge may be attached or fitted to the input mechanism in order to transfer holders from the cartridge into the incubator enclosure. A microprocessor 53 is connected to the mechanisms within the incubator enclosure 42. With multi-tasking, the microprocessor can provide several control functions, serving as a control means for the mechanisms which move and queue the holders within the incubator enclosure, as a way of controlling the timing of the taking of images by the camera, and as the counting means. The above referenced U.S. patent application Ser. No. 08/061,678, METHOD FOR THE EARLY DETECTION OF COLONY GROWTH, now U.S. Pat. No. 5,510,246, describes programming suitable for detecting and enumerating microbial colonies; the programming required to control the holder positioning means and the timing of the taking of video images depends on the user interface desired and on the exact physical arrangements and sizing of components, but the expedients required are well known to those of ordinary skill in the programming art.

Figure 5:
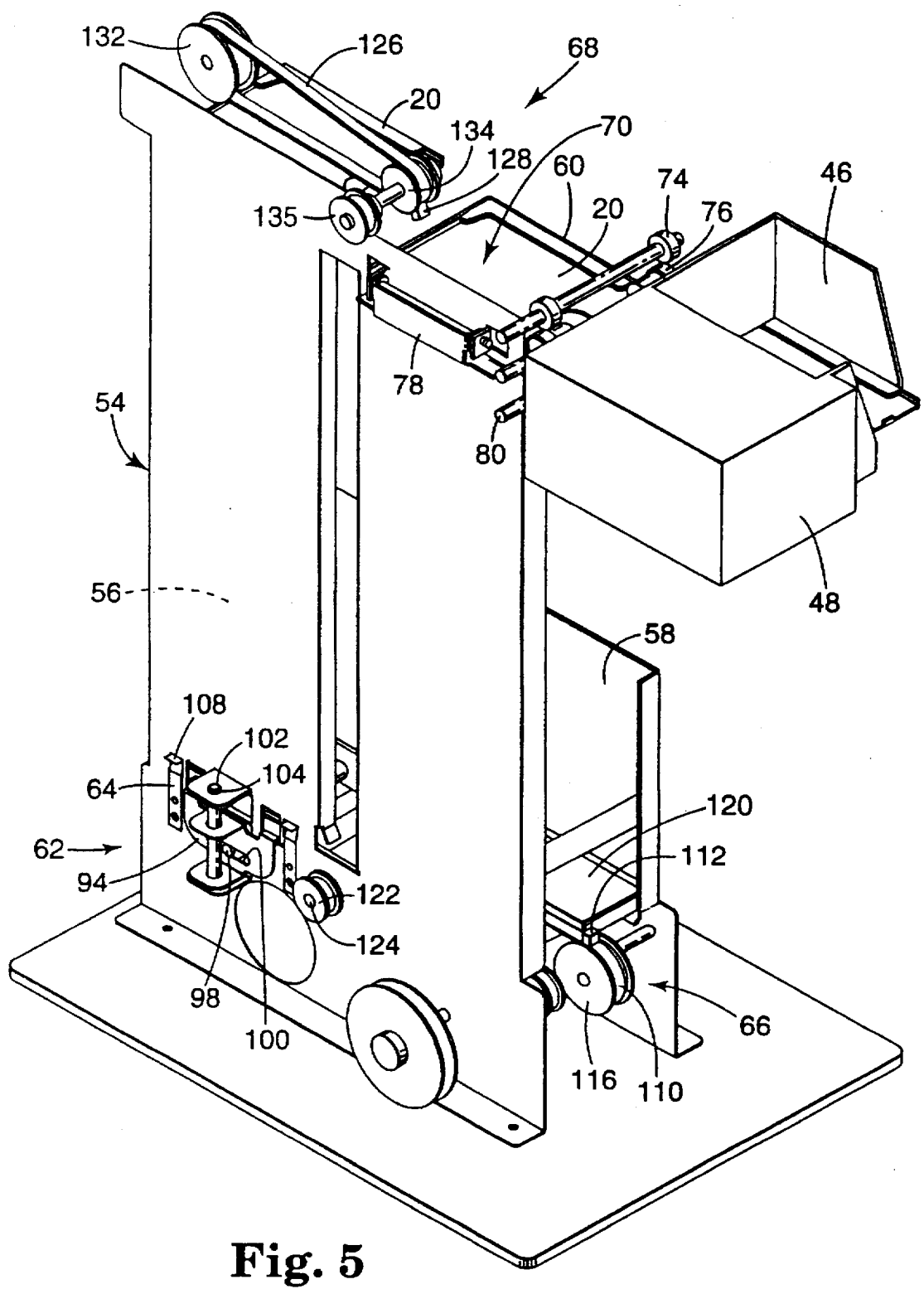
FIG. 5 is a cut-away perspective view of a holder positioning means of the apparatus of FIG. 4.

Referring to FIG. 5, a cut-away, perspective side view of the apparatus 40 of FIG. 4 is illustrated. Within incubator enclosure 42 is a frame 54, whose walls define a first queuing area 56 and a second queuing area 58. These queuing areas have a cross-section sized to support and contain a stack of trays 60 each sized to support one of the holders 20. While trays are not actually necessary for apparatus to work for its intended function, without them when adding or removing a holder from the stack in second queuing area 58, the viewing distance from the imaging means and the top holder in the stack changes and must be compensated for in other ways. With trays that are just slightly taller than the holders supporting the holders, the stack height is always the same no matter how many trays are filled with holders at the moment. A hoist means 62 is provided for lifting the stack of trays within the first queuing area 56, and a set of leaf springs 64 serve as a detent means so that the stack within the first queuing area may be lifted and held temporarily. A first conveyor means 66 is provided for displacing a tray 60 at the bottom of a stack within said second queuing area 58 to the bottom of the first queuing area 56 into the space provided when the rest of the stack of trays within the first queuing area 56 is being held in a raised position by the detent means 64. A second conveyor means 68 is provided for moving a tray 60 at the top of a stack of trays within the first queuing area 56 to the top of the second queuing area 56.

A stepper motor of conventional type, directed by microprocessor 53, is used to form a motive means which operates the various mechanical expedients above described in the proper order and manner to accomplish the task of moving trays bearing the appropriate holder to the predetermined position 70 when required for imaging. As will be described with more particularity below, a Geneva mechanism is a useful expedient for cycling the hoist means 62 and the proper time within the cycle of the first 66 and second 68 conveyor means. A conventional D.C. motor may substitute for a stepper motor if some arrangement (e.g., a notched wheel and a photodetector looking for the notch) is provided to signal the microprocessor 53 when the conveyors have finished their cycle.

Figure 13:
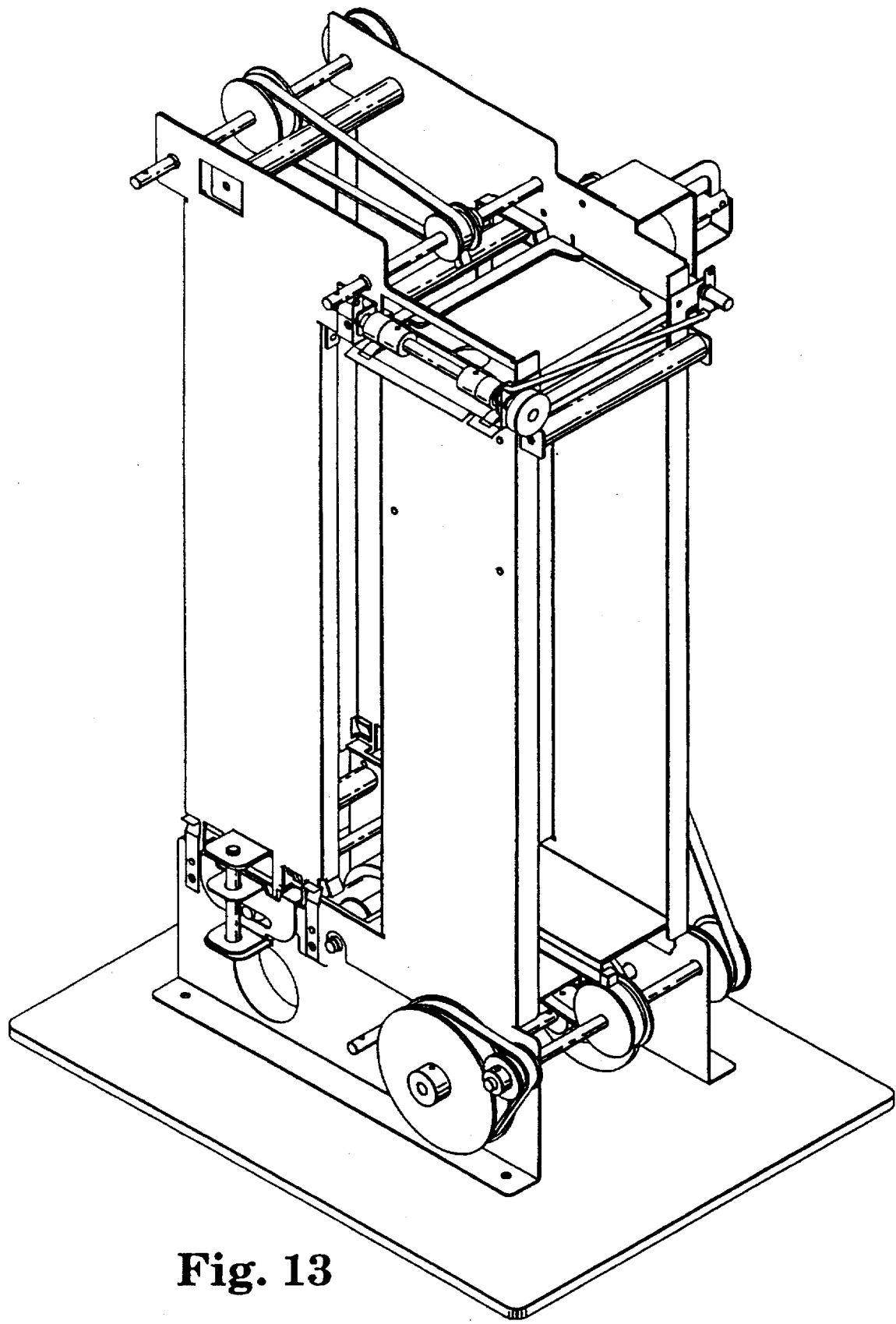
FIG. 13 is a perspective view of an alternative holder positioning means.
Figure 14:
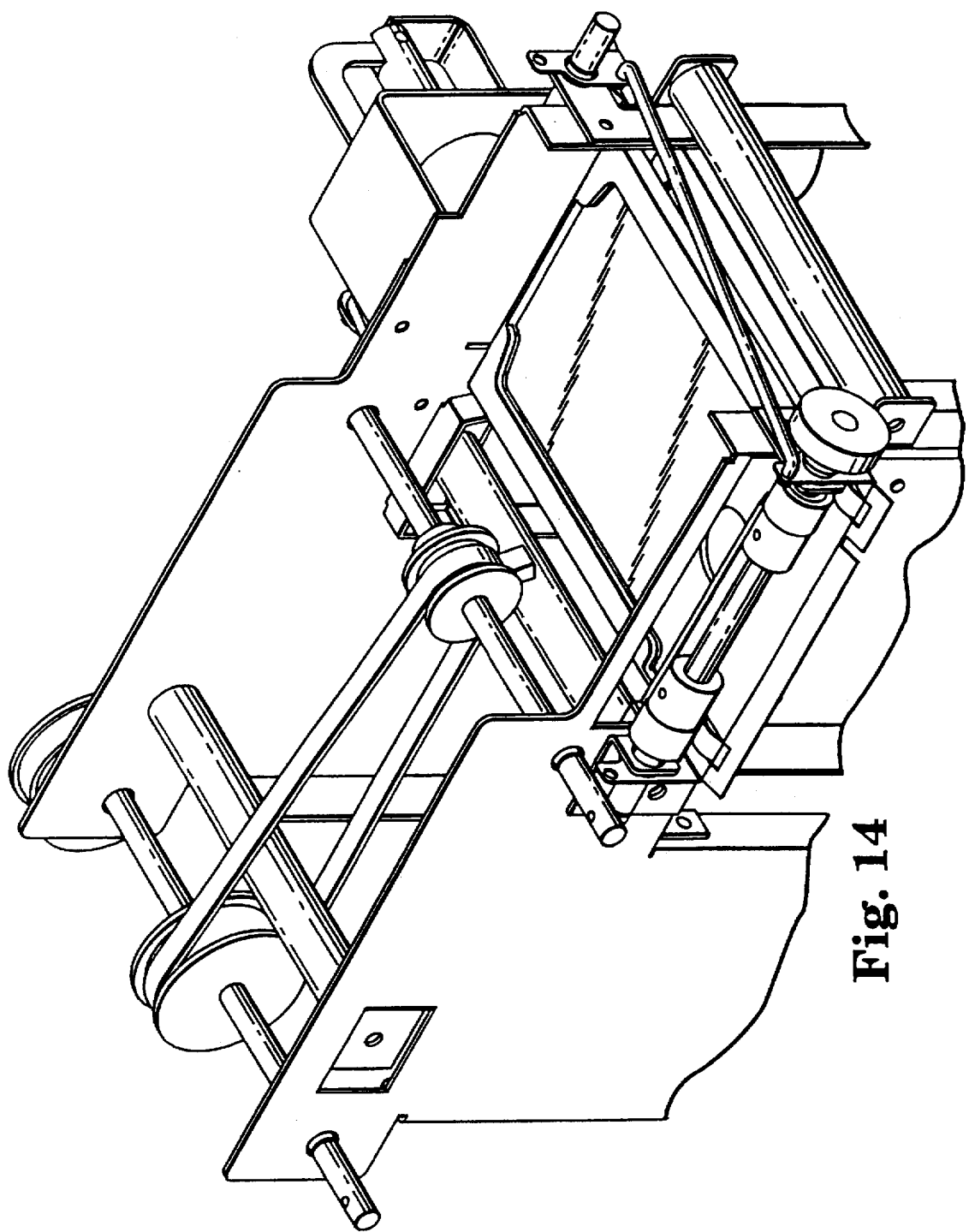
FIG. 14 is a cut-away perspective view of the holder of FIG. 13 highlighting a hoist and first conveyor means.

When activated, an input conveyor 50 (illustrated in FIG. 9) draws a holder 20 from a position at the bottom of a stack in shelf 46 into contact with drive wheels 74 and 76. The drive wheels 74 and 76 act to insert the new holder into an empty tray 60 within the stack of trays supported by the time 54 at the top of second queuing area 58. When it is desired to eject a holder 20 from the apparatus 40, ejection actuator 77 (illustrated in FIG. 8) is activated to move that holder into contact with drive wheels 76 and 80, which moves the holder out of its tray 60, through slot 82 (illustrated in FIG. 4) and into hopper 52. A simple solenoid, which extends to nudge the holder 20 into contact with the drive wheels 76 and 80, will be sufficient. An alternative input mechanism is illustrated in FIGS. 13 and 14. In this embodiment, a holder 20 is inserted in an empty tray 60 in a direction which is perpendicular to the input direction illustrated in FIGS. 5 and 9.

In order to very accurately position the tray 60 and holder 20 which is in predetermined position 70, a support cradle 78 is provided. The cradle 78 is closed to receive a tray 60 which has been delivered by the second conveyor means 68, and remains closed during the imaging of the holder 20. This careful positioning allows a very consistent focal length as each holder 20 is imaged several times. After the imaging is complete, cradle 78 opens and allows the tray 60 within it to fall a short distance onto the stack within second queuing area 58.

A driven motor shaft 124 attached to a main motor for providing energy to the first conveyor means 66, the second conveyor means 68, and the hoist means 62 can be seen. A system of timing belts, removed for visual clarity, connects motor shaft 124 to wheels 122, 135, and 106 (illustrated in FIG. 6), respectively.

Figure 6:
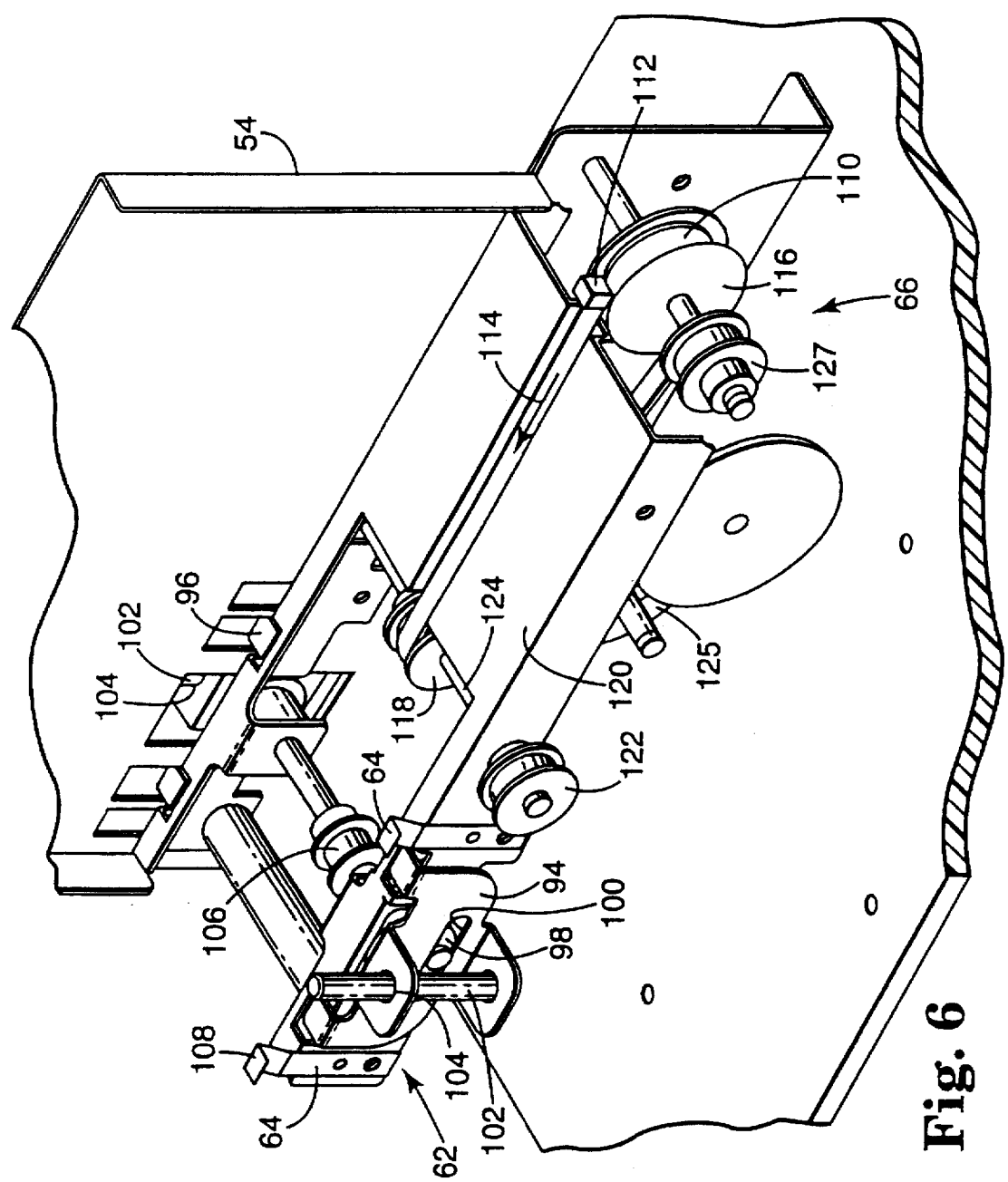
FIG. 6 is a cut-away perspective view highlighting a hoist and first conveyor means.

Referring to FIG. 6, a cut-away perspective view of hoist 62 and first conveyor means 66 at the bottom of the queuing areas is illustrated. Various structures, including a portion of the frame 54 have been removed for visual clarity. The hoist means 62 is conveniently constructed with a first 94 and second 96 lift trucks being moved via eccentric cams 98 acting on a slot 100 in each lift truck. The movement can be regulated by such expedients as a vertical rod 102 which is disposed within guide holes 104 on the lift trucks. Actuation of the hoist means 62 is conveniently accomplished via a timing belt around wheel 106. Once the lift trucks 94 and 96 have lifted the stack of trays upwards, the trays push past leaf springs 64, which then spring back to support the weight of the stack on their top surfaces 108, creating a gap at the bottom of the first queuing area 56, into which first conveyor means 66 can move one of the holders 20.

The first conveyor means 66 includes a belt 110 having a raised projection 112 on its outside, positioned so that when belt 110 is moved in direction 114 around pulleys 116 and 118, the projection 112 will engage a holder 20 lying on platform 120 and move it along the platform and onto lift trucks 94 and 96.

Motive power for the first conveyor 66 is conveniently provided via a timing belt engaging wheel 122, which turns pulley 118 via axle 124. A single motor can control the motion of the hoist means 62 via wheel 106 and the first conveyor means 66 via wheel 122 if the power for the hoist means 62 is transduced through a Geneva mechanism to rapidly move the hoist means through its cycle at the proper moment in the first conveyor means' cycle and be stationary at other times. Input power to the Geneva mechanism 125 (located under platform 120, is delivered via a timing belt (removed for visual clarity) around wheel 127.

Figure 7:
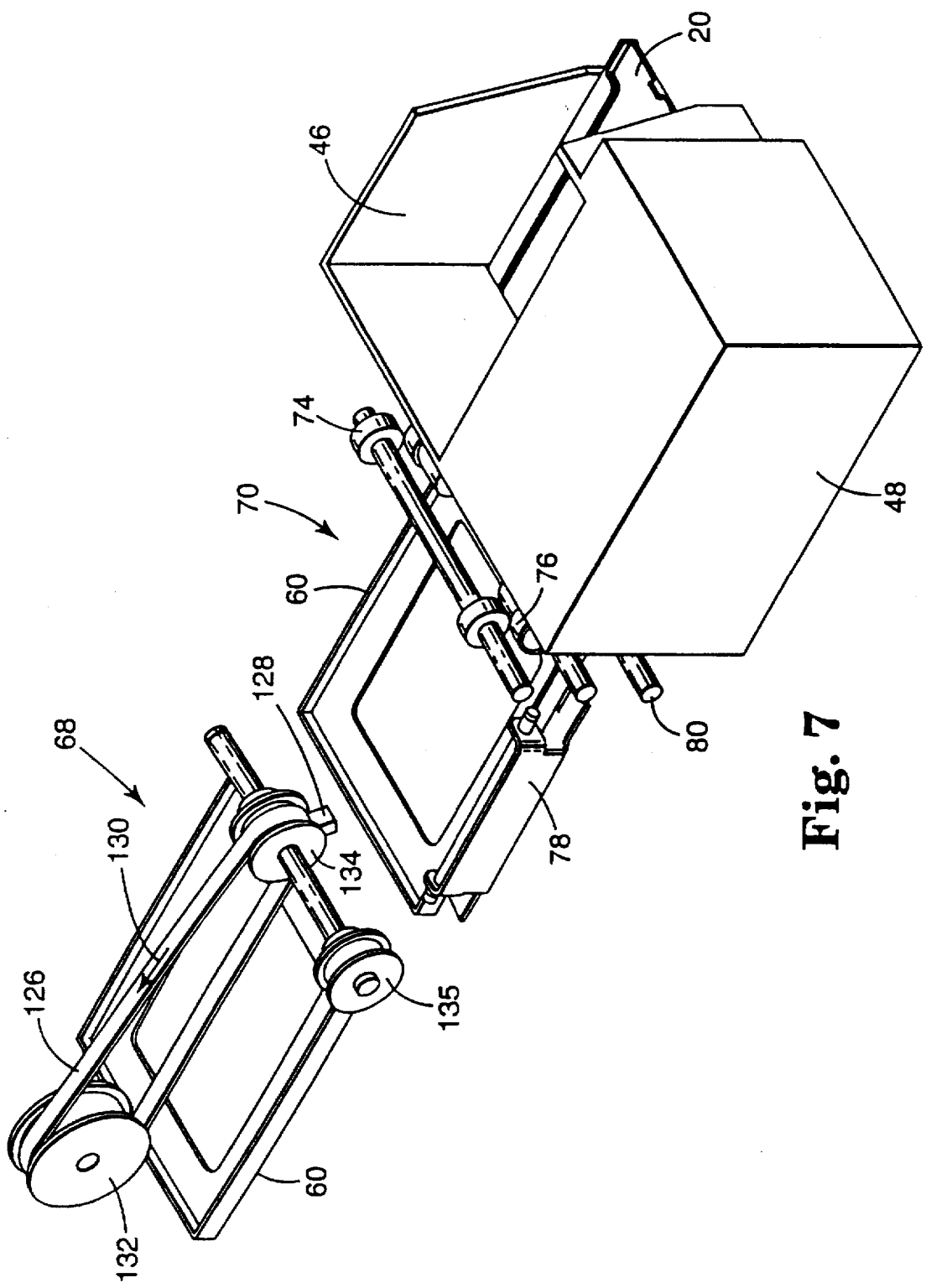
FIG. 7 is a cut-away perspective view highlighting a second conveyor means, the predetermined or viewing position, and the ejection actuator.

Referring to FIG. 7, a cut-away perspective view of second conveyor means 68, predetermined or viewing position 70, and cradle 78 at the top of the queuing areas are illustrated. Various structures, including a portion of the flame 54 have been removed for visual clarity. The second conveyor means 68 includes a belt 126 having a raised projection 128 on its outside, positioned so that when belt 126 is moved in direction 130 around pulleys 132 and 134, the projection 128 will engage a tray 60, which may or may not be supporting a holder 20, from the top of the stack in the first queuing area 56 and move it across to the top of the stack in the second queuing area 58. Motive power to move the second conveyor means 68 is supplied via a timing belt over wheel 135.

Referring to FIG. 8, a cut-away side view of the area depicted in FIG. 7 is illustrated. This view, particularly illustrates how a holder which has been moved by the input conveyor 50 (illustrated in FIG. 9) into contact with drive wheels 74 and 76 would be moved towards predetermined position 70 and inserted into an empty tray 60 within the stack of trays supported by the frame at the top of second queuing area 58. A microprocessor controlling the apparatus may be programmed to only activate the input conveyor 50 when an empty tray is in the predetermined position 70. This may be accomplished either by storing the status of the trays in data memory, or by using the imaging means to view the tray briefly to determine whether it is empty. When it is desired to eject a holder 20 from the tray 60 in position 70, ejection actuator 77 is activated to move that holder past the open end 137 of tray 60 and into contact with drive wheels 76 and 80, which moves the holder out of its tray 60 and from there out of the incubator enclosure 42.

Referring to FIG. 9, a cut-away top view of the area depicted in FIG. 8 is illustrated. The input conveyor 50 has moved a holder 20 along shelf 46 and into contact with drive wheel 74 so that holder 20 can be inserted into tray 60 in predetermined position 70. Input conveyor 50 is moved by a motor 136, under control of a microprocessor, when insertion of a new holder 20 into the apparatus is desirable. Motor 136 turns driven wheel 138, moving belt 140 around idlers 142 and 144, causing projection 146 to engage the end of holder 20, moving it towards drive wheel 74.

Figure 10:
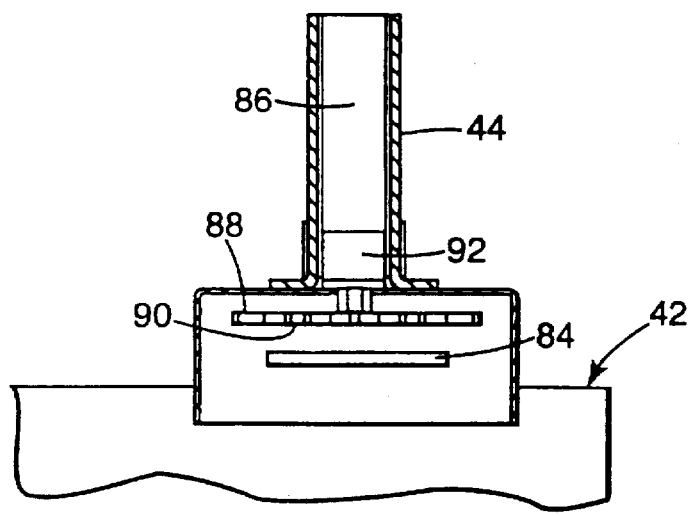
FIG. 10 is a cut-away side view of an imaging system of the apparatus of FIG. 4.

Referring to FIG. 10, a light source 84 is mounted above position 70 for producing light so as to strike the upper surface of a substantially planar substrate which is in a holder 20 in that position. A video camera 86 will be positioned so as to view a substantially planar substrate which is in a holder 20 in that predetermined position 70. A carousel 88 having several optical filters 90 is mounted between the predetermined position 70 and the video camera 86 to allow the image to be filtered when the chemistry of the growth and indicating media in the substrate is such that filtering the light reaching the video camera 86 enhances the ability of a computer to interpret the image generated. The carousel 88 is mounted on a stepper motor 92 so that it can be rotated as needed to provide any of several modes of filtering, or none.

Figure 11:
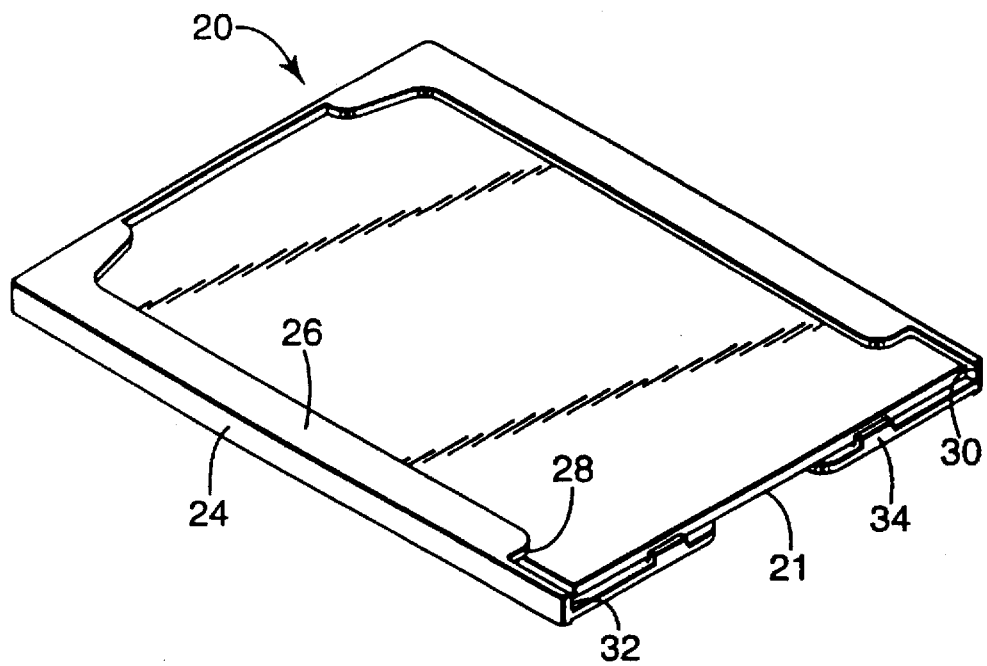
FIG. 11 is a perspective view of a holder with a substantially planar substrate installed.

Referring to FIG. 11, a perspective view of a holder 20 with a substantially planar substrate 21 installed is illustrated. The natural stiffness of the substantially planar substrate 21 causes it to be captured behind projections 34.

Figure 12:
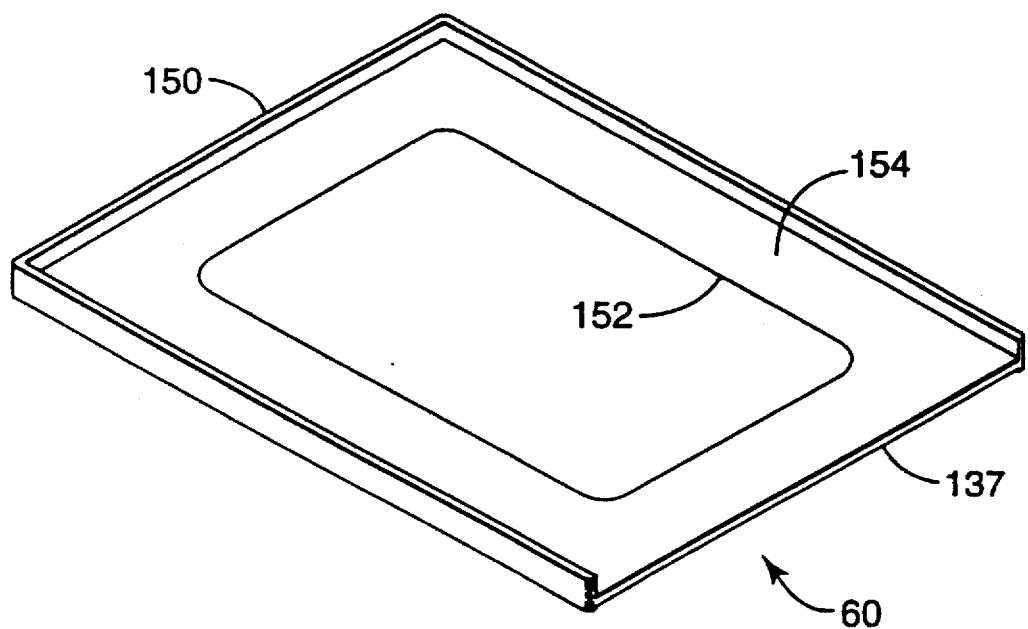
FIG. 12 is a top plan view of a tray which is used to support each holder within the holder positioning means.

Referring to FIG. 12, a top plan view of a tray 60 which is preferably used to support each holder 20 within the holder positioning means is illustrated. The tray 60 has a side wall 150 around three sides of its periphery, except for open end 137, which needs to be open to allow holder 20 to pass through and contact drive wheels 76 and 80 when it is desired to eject the holder from incubator enclosure 42. The trays are sized to fit within the first 56 and second 58 queuing areas, and sized to closely, but not bindingly, receive one of the holders 20. In order to reduce weight, a cut-out portion 152 may be provided in the bottom 154 of the tray.

DESCRIPTION OF THE PREFERRED EMBODIMENTS

Holders and trays suitable for use with the present invention can be fabricated from numerous materials, but rigid thermoplastic polymers which can be formed by injection molding are considered preferred. A certain amount of toughness in order to endure repeated handling by the operator and by the moving and queuing means is desirable, so plastics such as polycarbonate are considered particularly preferred.

Many different sorts of incubators are suitable for use with the present invention. In particular, the suitability of the "Model 2" gravity convection incubator commercially available from Precision Scientific, Inc. of Chicago, Ill. has been demonstrated by a physical trial.

With regard to the imaging system, a very steady light source is particularly desirable. Considered suitable for use with the present invention are "F6T5-CW" fluorescent tubes, commercially available from General Electric Co., driven by a precision power source, model "FX0416-2", commercially available from Mercron, of Richardson, Tex.

Charge coupled video cameras are considered particularly suitable for use with the present invention, such as the "XC-77" black-and-white camera commercially available from Sony Corp., of Japan. When filtering is desirable, band-pass interference filters are preferred, such as those commercially available from Corion, of Holliston, Mass.

A more complete description of disposable devices for culturing microorganism such as PETRIFILM culture plates is described in U.S. Pat. No. 4,565,783 to Hansen et al. Additional chemistries which may be used with the imaging means contemplated by the present invention are reported in U.S. Pat. No. 5,364,766 and U.S. patent applications Ser. No. 08/292,494 filed Aug. 18, 1994 now abandoned, and Ser. No. 08/292,784 filed Aug. 18, 1994, now U.S. Pat. No. 5,601,998.

While certain embodiments of the present invention have been described in detail herein and as shown in the accompanying Drawings, it will be evident that various further modifications are possible without departing from the scope of the invention. For example, alternative holder and queuing systems such as specifically adapted carousel apparatus may be combined with the presently described holders, imaging means, and counting means of this invention.

We claim:

1. An apparatus (40) for counting microorganism colonies on at least one disposable microorganism culturing medium having a substantially planar substrate (21); the substrate adapted to fit within and be supported by a holder (20) comprising:
   a) imaging means for detecting colonies on the substantially planar substrate (24); and
   b) holder positioning for storing and queuing one or more holders (20) and adapted for moving the holders sequentially into a predetermined position (70) relative to the imaging means; wherein the holder positioning means comprises
      i) a frame (54) defining a first queuing area (56) and a second queuing area (58);
      ii) hoist means (62) for adjusting the height of one or more holders (20) stacked within the first queuing area (56);
      iii) first conveyor means (66) for displacing a holder (20) at the bottom of a stack within the second queuing area (58) to the bottom of the first queuing area (56);
      iv) second conveyor means (68) for displacing a holder (20) at the top of a stack within the first queuing area (56) to the top of the second queuing area (58); and
      v) control means for operating the hoist means (62) and the first and second conveyor means (66, 68) in a predetermined sequence.

2. An apparatus according to claim 1 wherein the holder positioning means further comprises
   a) means for inserting an additional holder into a stack of the holders in the first or second queuing area (56, 58); and
   b) means for removing a selected holder from a stack of the holders in the first or second queuing area (56, 58).

3. An apparatus according to claim 1 wherein the holder positioning means further comprises a plurality of trays (60) sized to fit within the first and second queuing areas (56, 58), and sized to closely, but not bindingly, receive one of the holders (20), wherein each of the holders is supported within a stack of the trays within the first and second queuing areas.

4. An apparatus according to claim 1 wherein the holder positioning means further comprises an incubator (42) enclosing the frame (54).

5. An apparatus according to claim 1 wherein the imaging means comprises
   a) a light source (84) producing light striking an upper surface of a substantially planar substrate (21) which is in the holder (20) in the predetermined position (70); and
   b) a video camera (86) positioned so as to view a substantially planar substrate (21) which is in the holder (20) in the predetermined position (70).

6. A method of hinging microorganism colonies on at least one disposable microorganism culturing medium having a substantially planar substrate (21) comprising the steps of:
   a) providing one or more holders (20) adapted to support the substantially planar substrate (21);
   b) queuing and moving the holders (20) sequentially into a predetermined position (70) in an apparatus of claim 1 at two or more predetermined times; and
   c) imaging the substantially planar substrates (21) in the predetermined position at the predetermined times and storing information about the images so obtained.

7. A method according to claim 6 further comprising the step of incubating the substantially planar substrates (21) between the predetermined times.

8. A method according to claim 7 wherein the incubating step is performed within an incubator enclosure (42) having the holder positioning means therein and the queuing and moving step comprises queuing the holders (20) within a stack of trays (60) within the first and second queuing areas (56, 58).

9. A method according to claim 6 wherein the imaging step is performed with:
   a) a light source (84) producing light striking an upper surface of a substantially planar substrate (21) which is in the holder (20) in the predetermined position (70); and
   b) a video camera (86) positioned so as to view a substantially planar substrate (21) which is in the holder (20) in the predetermined position (70).

* * * * *

UNITED STATES PATENT AND TRADEMARK OFFICE
CERTIFICATE OF CORRECTION

PATENT NO.: 5,744,322
DATED: April 28, 1998
INVENTOR(S): Gary E. Krejcarek, Patrick A. Mach, Scott D. Morgan, and Thomas A. Turgeon It is certified that error appears in the above-identified patent and that said Letters Patent is hereby corrected as shown below:

Col. 8, line 47  "planar substrate (24)" should read --planar substrate (21)--

Col. 8, line 48  after "positioning" insert --means--

Col. 9, line 24  "planar substrate (24)" should read --planar substrate (21)--

Col. 9, line 26  "hinging" should read --imaging--

Signed and Sealed this

Fifteenth Day of May, 2001

Attest:

NICHOLAS P. GODICI

Attesting Officer    Acting Director of the United States Patent and Trademark Office